(12) United States Patent
Poullain et al.

(10) Patent No.: US 7,968,343 B2
(45) Date of Patent: Jun. 28, 2011

(54) CHEMICAL SENSORS COMPRISING ANILINE POLYSILOXANES AS SENSITIVE MATERIALS AND USE THEREOF FOR DETECTING OF ASSAYING NITRO COMPOUNDS

(75) Inventors: Didier Poullain, St Avertin (FR); Eric Pasquinet, St Avertin (FR); Lionel Hairault, Blere (FR)

(73) Assignee: Commissariat a l'Energie Atomique, Paris (FR)

( * ) Notice: Subject to any disclaimer, the term of this patent is extended or adjusted under 35 U.S.C. 154(b) by 569 days.

(21) Appl. No.: 11/576,836

(22) PCT Filed: Oct. 3, 2005

(86) PCT No.: PCT/FR2005/050805
§ 371 (c)(1),
(2), (4) Date: Apr. 6, 2007

(87) PCT Pub. No.: WO2006/037921
PCT Pub. Date: Apr. 13, 2006

(65) Prior Publication Data
US 2008/0070316 A1    Mar. 20, 2008

(30) Foreign Application Priority Data
Oct. 7, 2004 (FR) .................... 04 52302

(51) Int. Cl.
*G01N 33/00* (2006.01)
(52) U.S. Cl. ....... 436/72; 436/106; 436/107; 422/82.05; 422/82.07; 524/588
(58) Field of Classification Search .......... 524/730–731; 422/82.01, 82.02, 98, 68.1, 102
See application file for complete search history.

(56) References Cited

U.S. PATENT DOCUMENTS

| | | | |
|---|---|---|---|
| 4,634,756 A | 1/1987 | Mishra et al. | |
| 6,387,329 B1 * | 5/2002 | Lewis et al. | 422/98 |
| 6,630,560 B2 * | 10/2003 | McGill et al. | 528/25 |
| 2003/0165407 A1 * | 9/2003 | Aker et al. | 422/88 |
| 2005/0054116 A1 * | 3/2005 | Potyrailo et al. | 436/180 |

FOREIGN PATENT DOCUMENTS
JP       10176099    * 12/1996
WO   WO 02/08314 A1    1/2002

OTHER PUBLICATIONS

Garcia-Gonzalez et al. "Sensors: From Biosensors to the Electronic Nose". 2002. Grasas y Aceites. vol. 53. Fasc. 1. pp. 96-114.*
R. Zhou, et al., "Silicon-Containing Monomers, Oligomers and Polymers as Sensitive Coatings for the Detection of Organic Solvent Vapors", Sensors an Actuators B, XP004318438, vol. 26, No. 1-3, 1995, pp. 121-125.
Shawn M. Briglin, et. al, "Array Based Carbon Black-Polymer Composite Vapor Detectors for Detection of DNT in Environments Containing Complex Analyte Mixtures", Proceedings of SPIE, vol. 4394, 2001, pp. 912-921.

(Continued)

*Primary Examiner* — Yelena G Gakh
*Assistant Examiner* — David Weisz
(74) *Attorney, Agent, or Firm* — Oblon, Spivak, McClelland, Maier & Neustadt, L.L.P.

(57) ABSTRACT

A chemical sensor including a substrate having at least two faces, at least one of the faces being covered by a thin film that includes a sensitive material, and a means for measuring a change in a physical property of the sensitive material; and, methods of detecting the presence of a nitro compound with the chemical sensor.

23 Claims, 3 Drawing Sheets

OTHER PUBLICATIONS

R. A. McGill, et al., "The design of functionalized silicone polymers for chemical sensor detection of nitroaromatic compounds", Sensors and Actuators B, XP004208582, vol. 65, No. 1-3, Jun. 30, 2000, pp. 5-9.

Yoshiro Masuyama, et al., "Palladium-Catalyzed Allylic Amination of Allylic Alcohols with Tin(II) Chloride and Triethylamine", Chemistry Letters, 1995, pp. 1121-1122.

J. A. O. Sanchez-Pedreno, et al., "The Investigation of Coating Materials for the Detection of Nitrobenzene with Coated Quartz Piezoelectric Crystals", Analytica Chimica Acta, vol. 182, 1986, pp. 285-291.

T. P. Kofman et al., "5-Substituted 3-Nitro-1-vinyl-1,2,4-triazoles", Russian Journal of Organic Chemistry, vol. 37, No. 5, 2001, pp. 707-716.

* cited by examiner

CHEMICAL SENSORS COMPRISING ANILINE POLYSILOXANES AS SENSITIVE MATERIALS AND USE THEREOF FOR DETECTING OF ASSAYING NITRO COMPOUNDS

TECHNICAL FIELD

The present invention relates to chemical sensors comprising aniline-grafted polysiloxanes as sensitive materials and to the use of these sensors for detecting or assaying nitro compounds, in particular nitroaromatic compounds such as nitrobenzene (NE), dinitrobenzene DNB), trinitrobenzene (TNB), nitrotoluene (NT), dinitrotoluene (DNT), 2,4,6-trinitrotoluene (TNT), and the like.

Such sensors are useful for detecting explosives, whether for the purpose of ensuring safety in public places such as airports, for checking the legality of merchandise in circulation in a territory, for combating terrorism, for carrying out disarmament operations, for locating antipersonnel mines or even for decontaminating industrial or military sites.

They are also useful for protecting the environment, in particular for checking and monitoring atmospheric pollution and the quality of the ambient air in relatively confined spaces, and also for the monitoring, for security purposes, of industrial sites that manufacture, store and/or handle nitro compounds.

PRIOR ART

The detection of explosives is a problem of crucial interest, especially in terms of civil security.

At the present time, several methods are used for detecting the vapour of nitro compounds found in the composition of explosives, such as the use of "sniffer" dogs trained for this purpose, and the laboratory analysis, for example by chromatography coupled to a mass spectrometer or to an electron capture detector, of samples taken on site, or even infrared detection.

These methods prove in general to be very sensitive, this being of paramount importance for the detection of explosives, given the very low vapour concentration of nitro compounds near an explosive. However, the methods are not completely satisfactory.

Thus the use of "sniffer" dogs has the drawback of requiring the dogs and their masters to undergo lengthy training, and of being unsuitable for prolonged operations because the attention span of dogs is limited.

As regards the other methods, the sheer size of the apparatus that they use, their energy consumption and their operating costs all oppose the development of detection systems that are readily transportable and autonomous and, consequently, capable of being used on any type of site.

In recent years, great strides have been made in the development of sensors capable of detecting gaseous chemical species in real time. The operation of these sensors is based or the use of a film of a sensitive material, i.e. of a material having at least one physical property p (mass, temperature, electrical conductivity, absorbance, fluorescence, etc.) that is modified when it is in contact with the gaseous molecules sought, which amounts to a system capable of measuring, in real time, any variation in this physical property and thus demonstrating the presence of the gaseous molecules sought.

There are many advantages of chemical sensors over the abovementioned methods: instant results, possibility of miniaturization and, therefore portability, handlability and substantial autonomy, low manufacturing and operating costs, etc.

However, it is obvious that their performance levels are extremely variable, depending on the nature of the sensitive material used.

A number of sensitive materials have already been proposed for detecting gaseous nitro compounds, and more particularly nitroaromatic compounds, among which materials mention may be made of porous silicon, plant-derived carbon, polyethylene glycol, amines cyclodextrins, cavitands and fluorescent compounds.

Briglin et al. have also proposed, in *Proceedings of SPIE*, vol. 4394, 2001, 912-921, [1], the use, for detecting dinitrotoluene, of composites consisting of carbon black and poly [bis(cyanoallyl)siloxane] and of carbon black of polymethyloctadecylsiloxane in a multi-sensor system based on measuring a variation in the electrical conductivity of these composites.

Moreover, McGill et al. have described, in *Sens. Actuators B*65, 5-9, 2000, [2], and in PCT international application WO-A-02/08314 [3], the detection of some nitroaromatic compounds (nitrobenzene, dinitrotoluene, trinitrotoluene using a surface acoustic wave sensor comprising functionalized polysiloxanes as sensitive materials. These polysiloxanes are functionalized with a phenyl group substituted with one or more hexafluoroisopropanol (HFIP) groups.

According to McGill et al., the presence of this or these HFIP group(s) is directly responsible for the sensitivity of the sensor to nitroaromatic compounds due to the fact that it allows the formation of hydrogen bonds between the hydroxyl function present in these groups and the nitro group of the nitroaromatic compounds.

Now, within the framework of their work on the development of sensors intended more especially for detecting explosives the inventors have noted that sensors using, as sensitive materials polymers based on siloxanes functionalized with a phenyl group substituted with one or more (primary, secondary and/or tertiary) amine functions detect nitro compounds, and in particular nitroaromatic compounds, with a much greater sensitivity than sensors using the polysiloxanes recommended by McGill et al., including in the case where this phenyl group does not comprise a pendant HFIP group.

It is this observation that forms the basis of the invention.

SUMMARY OF THE INVENTION

A subject of the invention is a chemical sensor which comprises, as sensitive material, at least one polymer comprising a siloxane repeating unit of formula (I) below:

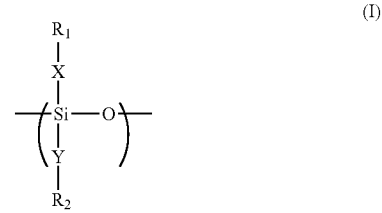

in which:
X and Y represent, independently of one another, a single bond or a saturated or unsaturated, linear, branched or cyclic hydrocarbon group comprising from 1 to 30 carbon atoms and, optionally, one or more heteroatoms, and/or one or more chemical functions containing at least one heteroatom, and/or one or more aromatic or heteroaromatic groups;

R$_1$ represents an aniline group corresponding to formula (II) below:

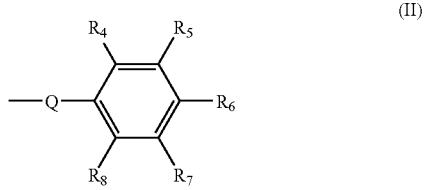

in which:
Q represents a single bond, a —CH$_2$— group, or else an —NR$_3$— group in which R$_3$ represents a hydrogen atom or a saturated or unsaturated, linear hydrocarbon group comprising from 1 to 10 carbon atoms;

R$_4$ to R$_8$ represent, independently of one another, a hydrogen atom, a chemical function containing at least one heteroatom, or else a saturated or unsaturated, linear, branched or cyclic hydrocarbon group comprising from 1 to 30 carbon atoms and, optionally, one or more heteroatoms, and/or one or more chemical functions containing at least one heteroatom, and/or one or more aromatic or heteroaromatic groups;

and in which, when Q is a single bond or a —CH$_2$— group, then at least one of the radicals R$_4$ to R$_8$ represents an amino group —N$_9$R$_{10}$ in which R$_9$ and R$_{10}$ represent, independently of one another, a hydrogen atom, a chemical function containing at least one heteroatom, or else a saturated or unsaturated, linear, branched or cyclic hydrocarbon group comprising from 1 to 30 carbon atoms and, optionally, one or more heteroatoms, and/or one or more chemical functions containing at least one heteroatom, and/or one or more aromatic or heteroaromatic groups;

R$_2$ represents a hydrogen atom or an aniline group of formula (II) as defined above.

In formula (I) above, when X and/or Y represent(s) a single bond, then R$_1$ and/or R$_2$ is (are) directly attached to the silicon atom by a covalent bond.

Similarly, when R$_1$ represents a group of formula (II) in which Q represents a single bond, then the phenyl ring of this group is directly attached to X or to the silicon atom if X itself represents a single bond, while, when R$_2$ represents a group of formula (II) in which Q represents a single bond, then the phenyl ring of this group is directly attached to Y or to the silicon atom if Y itself represents a single bond.

Moreover, when X and/or Y represent(s) a hydrocarbon group comprising at least two carbon atoms and this group contains one or more heteroatoms, and/or one or more chemical functions, and/or one or more aromatic or heteroaromatic groups, then this or these heteroatom(s), this or these chemical function(s) and this or these aromatic or heteroaromatic group(s) can form a bridge within this group or be borne laterally by it, while, when R$^1$, R$^2$, R$^3$, R$^4$, R$^5$, R$^6$, R$^7$, R$^8$, R$^9$, R$^{10}$, R$^{11}$ and/or R$^{12}$ represent a hydrocarbon group comprising at least two carbon atoms and this group contains one or more heteroatoms, and/or one or more chemical functions, and/or one or more aromatic or heteroaromatic groups then this or these heteroatom(s), this or these chemical function(s) and this or these aromatic or heteroaromatic group(s) can form a bridge within this group, be borne laterally by it or else be located at its end.

In accordance with the invention, the hydrocarbon group(s) that are part of formulae (I) and (II) above, when they are cyclic and unsaturated, can just as easily be aromatic groups (or heteroaromatic groups if they contain one or more heteroatoms in their ring or in one of the rings of which they are formed), as non-aromatic groups (cycloalkene or cycloalkene groups).

By way of examples of aromatic groups that can be used in the invention, mention may be made of cyclopentadienyl, phenyl, benzyl, biphenyl, phenylacetylenyl pyrene or anthracene groups, while, by way of examples of heteroaromatic groups, mention may be made of furanyl, pyrrolyl, thiophenyl, oxazolyl, pyrazolyl, thiazolyl, imidazolyl triazolyl, pyridinylpyranyl, quinolinyl, pyrazinyl and pyrimidinyl groups.

The heteroatom(s) may be any atom other than carbon or hydrogen, for instance an oxygen, sulphur, nitrogen fluorine, chlorine, phosphorous, boron or else silicon atom, oxygen, sulphur and nitrogen atoms being preferred.

The chemical function(s) containing at least one heteroatom can in particular be chosen from the functions —COOH, —COOR$_{11}$, —CHO, —CO—, —OH, —OR$_{11}$, —SH, —SR$_{11}$, —SO$_2$R$_{11}$, —NH$_2$, —NHR$_{11}$, —NR$_{11}$R$_{12}$, —CONH$_2$, —CONHR$_{11}$, —CONR$_{11}$R$_{12}$, —C(Hal)$_3$, —OC(Hal)$_3$, —C(O)Hal, —CN, —COOCHO and —COOCOR$_{11}$, in which:

R$_{11}$ represents a saturated or unsaturated, linear, branched or cyclic hydrocarbon group comprising from 1 to 30 carbon atoms, or a covalent bond in the case where said chemical function forms a bridge in a C$_2$ to C$_{30}$ hydrocarbon group;

R$_{12}$ represents a saturated or unsaturated, linear, branched or cyclic hydrocarbon group comprising from 1 to 30 carbon atoms, it being possible for this group to be identical to or different from the hydrocarbon group represented by R$_{11}$; while Hal represents a halogen atom, for example a fluorine, chlorine or bromine atom.

According to a first preferred embodiment of the invention, the siloxane repeating unit corresponds to formula (I) in which R$_1$ represents an aniline group of formula (IIa), (IIb) or (IIc) below:

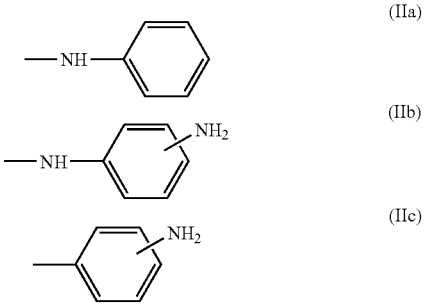

In formulae (IIb) and (IIc), the primary amine group of the aniline group may be located in the ortho-, meta- or para-position with respect to the element to which the phenyl ring is attached, i.e., in the case of formula (IIb), with respect to the secondary amine group of this aniline group and, in the case of formula (IIc), with respect to X or to the silicon atom if X represents a single bond.

According to another preferred embodiment of the invention, the siloxane repeating unit corresponds to formula (I) in which X represents an alkylene group comprising from 1 to 10 carbon atoms, and preferably a propylene group, Y represents an alkylene group containing from 1 to 3 carbon atoms and preferably a methylene group, while $R_2$ represents a hydrogen atom.

Thus, among the siloxane repeating units of formula (I), preference is in particular given to those in which X represents a propylene group, $R_1$ represents an aniline group of formula (IIa), (IIb) or (IIc) and Y represents a methylene group, while $R_2$ represents a hydrogen atom, and among these, those which correspond to formulae (Ia), (Ib) or (Ic) below:

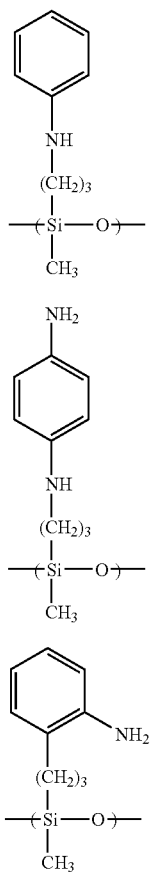

In accordance with the invention, the polymer may be a homopolymer, in which case it consists of just one and the same siloxane repeating unit of formula (I).

Such a homopolymer is, for example, a homopolymer formed by the repeating unit of formula (Ia).

As a variant, the polymer may also be a copolymer, in which case it can just as easily consist of various siloxane repeating units all corresponding to formula (I), as comprise one or more siloxane repeating units of formula (I) and one or more other repeating units, which may or may not be siloxane units.

According to yet another preferred embodiment of the invention, the polymer is a copolymer which comprises two different siloxane repeating units a first siloxane unit corresponding to formula (I) above, in which X, Y, $R_1$ and $R_2$ have the same meaning as above, and a second siloxane unit corresponding to formula (III) below:

in which W and Z, which may be identical or different, represent a hydrogen atom, or a saturated or unsaturated, linear, branched or cyclic hydrocarbon group comprising from 1 to 30 carbon atoms.

Preferably, the second siloxane unit is a dihydrosiloxane (W=Z=H) a methylhydrosiloxane (one of W and of Z=H while the other=$CH_3$) or a dimethylsiloxane (W=Z=$CH_3$), the latter unit being preferred.

Examples of such copolymers are in particular copolymers comprising:
  a first siloxane unit of formula (Ia) and a second dimethylsiloxane unit; or
  a first siloxane unit of formula (Ib) and a second dimethylsiloxane unit; or else
  a first siloxane unit of formula (Ic) and a second dimethylsiloxane unit.

In accordance with the invention, these polymers may be random, alternating or block copolymers, but they are preferably random copolymers.

Moreover, preference is given to copolymers in which the first siloxane unit represents, by number, approximately 47% of the repeating units forming these copolymers, while the second siloxane unit represents, by number, approximately 53% of the repeating units forming said copolymers.

Whether a homopolymer or a copolymer is involved, the molecular mass of the polymer by mass is generally greater than or equal to 200 g/mol, and is preferably from 200 to 100 000 g/mol, and even better still from 1000 to 10 000 g/mol.

The polymer may also comprise a repeating unit derived from a monomer of the ethylene/propylene, ethylene oxide styrene, vinylcarbazole or vinyl acetate type, which are capable of giving it better mechanical properties, especially when it is desired to use it in the form of a thin film.

According to yet another preferred embodiment of the invention, the polymer is in the form of a thin film that covers one or both faces of a substrate suitably chosen as a function of the physical property of the sensitive material whose variations are intended to be measured by this sensor.

As a variant, the polymer may also be in a bulk form, for instance a cylinder having a certain porosity so as to make all of the molecules forming said polymer available to the nitro compounds.

When it is in the form of a thin film, this film is preferably from 10 angstroms to 100 microns thick.

Such a film may in particular be obtained by spraying or by spin-coating a solution containing the polymer onto the substrate, or by dip-coating of the substrate in a solution containing the polymer.

The substrate and the measuring system of the sensor are chosen according to the physical property of the polymer whose variations induced by the presence of nitro compounds are intended to be measured by the sensor.

In the case in point the variations in mass of the polymer prove to be particularly advantageous to measure. Thus, the sensor is preferably a gravimetric sensor.

By way of examples of gravimetric sensors, mention may be made of sensors of the quartz microbalance type, surface acoustic wave (SAW) sensors, such as Love wave sensors and Lamb wave sensors, and also microlevers.

Among the gravimetric sensors that are more particularly preferred are quartz microbalance sensors. Sensors of this type, the operating principle of which has been described by Sanchez-Pedrono et al., in *Anal. Chem. Acta* vol. 182, 1986, 285 [4], comprise, schematically a piezoeleotric substrate (or resonator), generally a quartz crystal covered on its two faces with a layer of metal, for example gold or platinum, which serves as an electrode. Since the sensitive material covers one or both faces of the substrate, any variation in the mass of this material is reflected by a variation in the vibration frequency of the substrate.

Of course, it is also possible to use a polymer as defined above, as sensitive material in sensors designed to measure variations in a physical property other than the mass, for instance resistive sensors based on the measurement of variations in electrical conductivity or optical sensors based on the measurement of variations in fluorescence, in luminescence, in absorbance in the visible UV range or in wavelength in the infrared range.

In fact, although the polymers comprising a siloxane repeating unit of formula (I) are not electrically conducting polymers, they may be mixed with one or more conductive fillers so as to obtain composites exhibiting an electrical conductivity suitable for use as sensitive materials of resistive sensors. These conductive fillers may, for example, be particles of carbon black or metal powders (Cu, Pd, Au, Pt, etc.) or metal oxide powders $V_2O_3$, TiO, etc.).

In the case of an optical sensor, it is possible either to use an intrinsic optical property of the polymer when the latter has one (absorbance, IR spectrum, etc.), or to confer on this polymer a particular optical property by coupling with an appropriate marker, for example a fluorescent or luminescent marker.

The chemical sensor according to the invention may be integrated into a multisensor, i.e. into a device combining several individual sensors, it being possible for these individual sensors to have different sensitive materials, substrates and/or measuring systems.

Thus, a subject of the invention is a multisensor comprising one or more individual sensors assembled together and in which at least one of these individual sensors is a chemical sensor as defined above.

The chemical sensors according to the invention have been found to have many advantages, in particular:
  an ability to specifically detect nitro compounds, and in particular nitroaromatic compounds, with a very high sensitivity since they are capable of detecting their presence at concentrations of less than one ppm (part per million) and even one tenth of a ppm,
  rapid response and reproducibility of this response,
  stability of performance levels over time and, consequently, a very satisfactory service life,
  ability to function continuously,
  manufacturing cost compatible with a production of sensors in series, a very small amount of polymer (i.e. in practice, a few mg) being necessary for the manufacture of a sensor, and
  possibility of being miniaturized and, consequently, of being readily transportable and handlable on all types of sites.

A subject of the invention is also the use of a chemical sensor as defined above, for detecting or assaying one or more nitro compounds, it being possible or these compounds to just as easily be in solid, liquid or gaseous (vapour) form, but said compounds preferably being in gaseous form.

In accordance with the invention, the nitro compound(s) intended to be detected or assayed are chosen from nitroaromatic compounds, nitramines, nitrosamines and nitric esters.

By way of examples of nitroaromatic compounds, mention may be made of nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene or trinitrophenol (or picric acid).

Examples of nitramines include cyclotetramethylenetetranitramine (or octogen), cyclotrimethylenetrinitramine (or hexogen) and trinitrophenylmethylnitramine (or tetryl), while the nitrosamines are, for example, nitrosodimethylamine.

As regards the nitric esters, they are, for example, pentrite, ethylene glycol dinitrate, diethylene glyco dinitrate, nitroglycerine or nitroguanidine.

According to yet another preferred embodiment of the invention, the sensor is used for detecting or assaying explosives.

The invention will be understood more clearly in the light of the further description, which relates to examples of preparation of aniline-comprising polysiloxanes that can be used as sensitive materials in chemical sensors, and also to examples of production of chemical sensors comprising such polysiloxanes as sensitive materials and examples demonstrating their properties.

Of course, these examples are given merely by way of illustration of the subject of the invention and do not in any way constitute a limitation of this subject.

DETAILED DISCLOSURE OF SPECIFIC EMBODIMENTS

Example 1

Preparation of Aniline-Grafted Polysiloxanes

Figure 1:
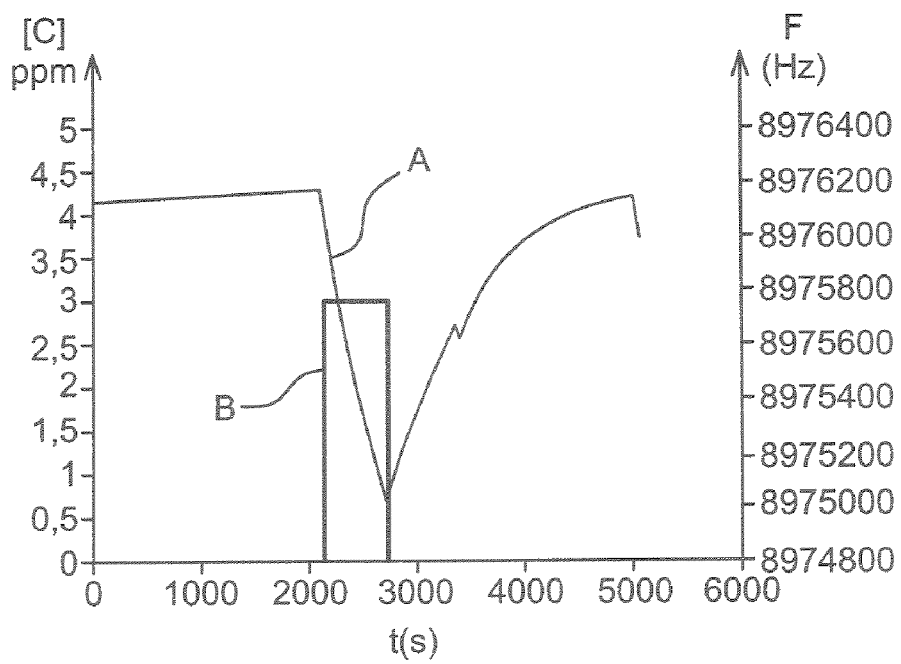
FIG. 1 represents the change in the vibration frequency of the quartz crystal of a first example of a sensor according to the invention when this sensor is exposed to air and to 2,4-dinitrotrifluoromethoxybenzene (DNTFMB) vapours.

Four polymers, respectively denoted hereinafter A, B, C and D, and having the following compositions:

Polymer A:
  Homopolymer of a repeating unit of formula (Ia);
Polymer B:
  Random copolymer formed from a repeating unit of formula (Ia) and a dimethylsiloxane repeating unit in a ratio of 0.47 unit of formula (Ia) to 0.53 dimethylsiloxane unit;
Polymer C:
  Random copolymer formed from a repeating unit of formula (Ib) and a dimethylsiloxane repeating unit in a ratio of 0.47 unit of formula (Ib) to 0.53 dimethylsiloxane unit;
Polymer D:
  Random copolymer formed from a repeating unit of formula (Ic) and a dimethylsiloxane repeating unit in a ratio of 0.47 unit of formula (Ic) to 0.53 dimethylsiloxane unit;
are prepared by modifying polysiloxanes comprising, in the case of the preparation of polymer A, only a methylhydrosiloxane repeating unit of formula (IV) below:

(IV)

and, in the case of the preparation of polymers B, C and D, a methylhydrosiloxane repeating unit and a dimethylsiloxane repeating unit in a ratio of 0.47 methylhydrosiloxane unit to 0.53 dimethylsiloxane unit.

These polysiloxanes are in particular available from the company ABCR under the references HMS 992 and HMS 501.

The modification consists in coupling an allyl amino compound of formula (V) below:

(V)

in which R represents one of the following groups:

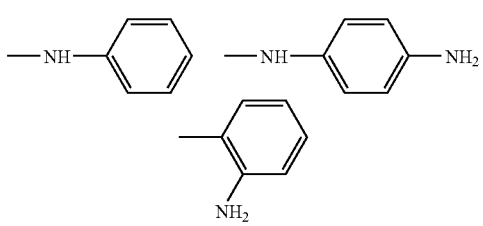

to the repeating unit of formula (IV) by catalytic hydrosilylation according to the following reaction scheme:

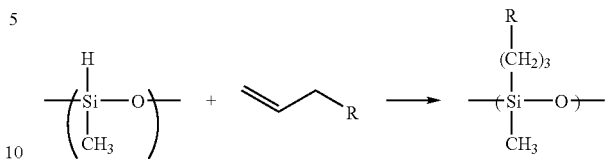

This hydrosilylation is carried out as a solid process for polymers A and B, and in solution for polymers C and D.

In the case of polymers A and B, the allylic monomer (1.5 mmol) of N-allylaniline, available from Sigma-Aldrich under the reference A2,900-3) is heated to 80° C. under a nitrogen stream. The catalyst (25 µl of a solution of hexachloroplatinic acid ($H_2PtCl_6$), available from Sigma-Aldrich under the reference 52,098-6 in isopropanol at 0.84% by mass or 20 µl of Karstedt catalyst, available from Sigma-Aldrich under the reference 47,951-9) is added. After stirring for 15 minutes, the polysiloxane is added dropwise and the solution is heated at 105° C. for 5 hours. After filtration over activated carbon, the product is purified by removing the volatile compounds by distillation under vacuum.

Polymers A and B are thus obtained in the form of orange oils, with a yield of 96% and 93%, respectively.

In the case of polymers C and D, the allylic monomer (1.5 mmol of 4-amino-N-allylaniline, synthesized as described by Kaufman et al., *Russian J. Org. Chem.*, vol. 37, 5, 2001, 707, [5], for polymer C, and 1.5 mmol of 2-allylaniline, synthesized as described by Tsuji et al., *Chem., Lett.*, 1995, 1121-1122, [6], for polymer D) in solution in 3 ml of toluene is heated to 80° C. under a nitrogen stream. The catalyst (0.84% by mass of $H_2PtCl_6$ in solution in isopropanol or 20 µl of Karstedt catalyst) is added. After stirring for 15 minutes, the polysiloxane is added dropwise and the solution is heated at 105° C. for 5 hours. After filtration over activated carbon, the product is purified by removing the volatile compounds by distillation under vacuum.

Polymer C is thus obtained in the form of a black oil, with a yield of 28%, and polymer D is obtained in the form of a brown oil, with a yield of 84%.

Example 2

Detection of DNTFMB by a Sensor According to the Invention

In this example, a quartz microbalance sensor is produced by covering the two faces of an AT cut quartz crystal, with a vibration frequency of 9 MHz, provided with two circular gold measurement electrodes (model QA9RA-50, AMETEK PRECISION INSTRUMENTS) with a thin film of polymer B prepared in accordance with Example 1.

This film is deposited on each face of the quartz crystal by spraying a 5 g/l solution of polymer B in chloroform 20 times each lasting 0.3 second.

The change in the vibration frequency of the quartz crystal due to this coating was 9.9 kHz.

The sensor is exposed successively to:
air for 2100 seconds,
DNTFMB at a concentration of a 3ppm in air for 600 seconds, and
air for 2310 seconds,
the air and the DNTFMB being at ambient temperature.

FIG. 1 illustrates the change in the vibration frequency of the quartz crystal over the course of these exposures.

In this figure, curve A represents the values of the vibration frequency (F) of the quartz crystal expressed in Hz (hertz), as a function of time (t), expressed in seconds, while curve B represents the values of the concentration of DNTFMB ([C]), expressed in ppm, also as a function of time.

Example 3

Detection of DNTFMB by a Sensor According to the Invention

In this example, a quartz microbalance sensor was produced by covering the two faces of a quartz crystal identical to that used in Example 2, with a thin film of polymer A prepared in accordance with Example 1.

This film is deposited on each face of the quartz crystal by spraying a 10 g/l solution of polymer A in chloroform 8 times, each lasting 0.3 second.

The change in the vibration frequency of the quartz crystal due to this coating is 9.5 kHz.

The sensor is exposed successively to:
air for 460 seconds,
DNTFMB at a concentration of 3 ppm in air for 600 seconds, and
air for 1800 seconds,
the air and the DNTFMB being at ambient temperature.

Figure 2:
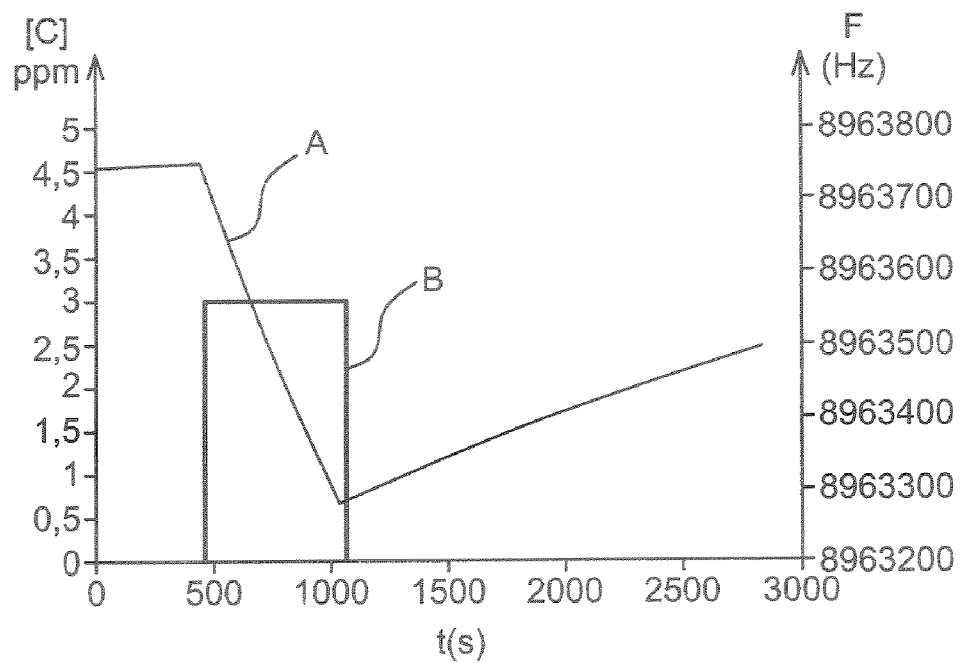
FIG. 2 represents the change in the vibration frequency of the quartz crystal of a second example of a sensor according to the invention when this sensor is exposed to air and to DNTFMB vapours.

FIG. 2 illustrates the change in the vibration frequency of the quartz crystal over the course of these exposures.

In this figure, curve A represents the values of the vibration frequency (F) of the quartz crystal, expressed in Hz (hertz), as a function of time (t), expressed in seconds, while curve B represents the values of the concentration of DNTFMB ([C]), expressed in ppm, also as a function of time.

Example 4

Demonstration of the Selectivity of a Sensor According to the Invention for Nitro Compounds with Respect to Solvents In this example, a quartz microbalance sensor is produced by covering the two faces of a quartz crystal identical to that used in Example 2, with a thin film of polymer C prepared in accordance with Example 1.

This film is deposited on each face of the quartz crystal by spraying a 5 g/l solution of polymer C in chloroform 23 times, each lasting 0.4 second.

The change in the vibration frequency of the quartz crystal due to this coating is 10 kHz.

The sensor is exposed successively to:
air for 1550 seconds,
DNTFMB at a concentration of 3 ppm in air for 600 seconds,
air for 1820 seconds,
DNTFMB at a concentration of 3 ppm in air for 600 seconds,
air for 1650 seconds,
toluene at a concentration of 38 000 ppm in air for 600 seconds,
air for 130 seconds,
methyl ethyl ketone at a concentration of 126 000 ppm in air for 600 seconds,
air for 170 seconds,
ethanol at a concentration of 79 000 ppm in air for 170 seconds, and
air for 50 seconds,
the air, the DNTFMB, the toluene, the methyl ethyl ketone and the ethanol being at ambient temperature.

Figure 3:
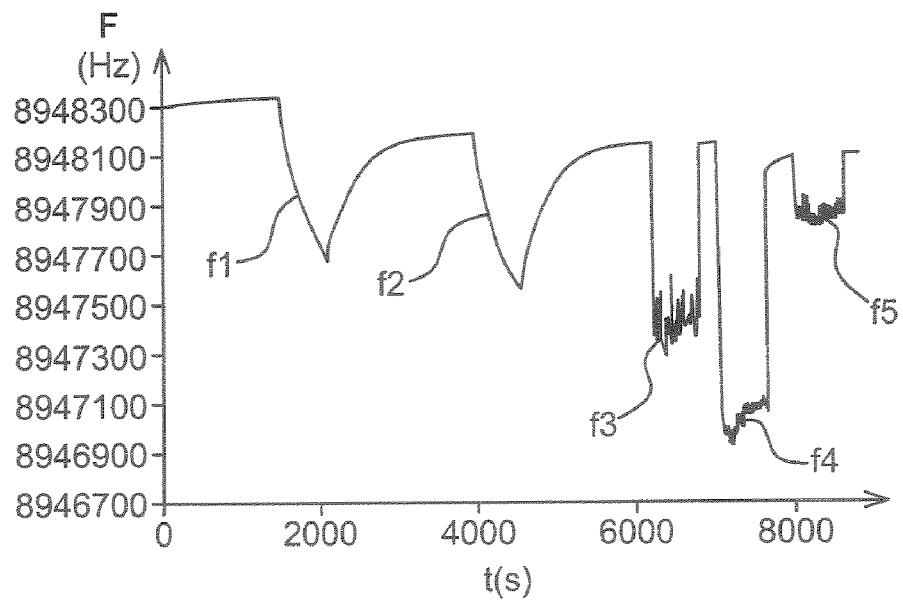
FIG. 3 represents the change in the vibration frequency of the quartz crystal of a third example of a sensor according to the invention when this sensor is exposed to air and to DNTFMB vapours, toluene vapours, methyl ethyl ketone vapours and ethanol vapours.

FIG. 3 represents the values of the vibration frequency (F) of the quartz crystal, expressed in Hz, as a function of time (t), expressed in seconds, the arrows f1 and f2 indicating the exposures to DNTFMB, the arrow f3 the exposure to toluene, the arrow f4 the exposure to methyl ethyl ketone and the arrow f5 the exposure to ethanol.

This figure shows that exposure of the sensor according to the invention to solvents such as toluene, methyl ethyl ketone or ethanol, does not bring about a response of the sensor that is comparable to that obtained when the latter is exposed to a nitro compound.

Example 5

Detection of DNTFMB by a Sensor According to the Invention

In this example, a quartz microbalance sensor is produced by covering the two faces of a quartz crystal identical to that used in Example 2, with a thin film of polymer D prepared in accordance with Example 1.

This film is deposited on each face of the quartz crystal by spraying a 5 g/l solution of polymer D in chloroform 16 times, each lasting 0.3 second.

The change in the vibration frequency of the quartz crystal due to this coating is 10 kHz.

The sensor is exposed successively to:
air for 1224 seconds,
DNTFMB at a concentration of 3 ppm in air for 600 seconds, and
air for 1480 seconds,
the air and the DNTFMB being at ambient temperature.

Figure 4:
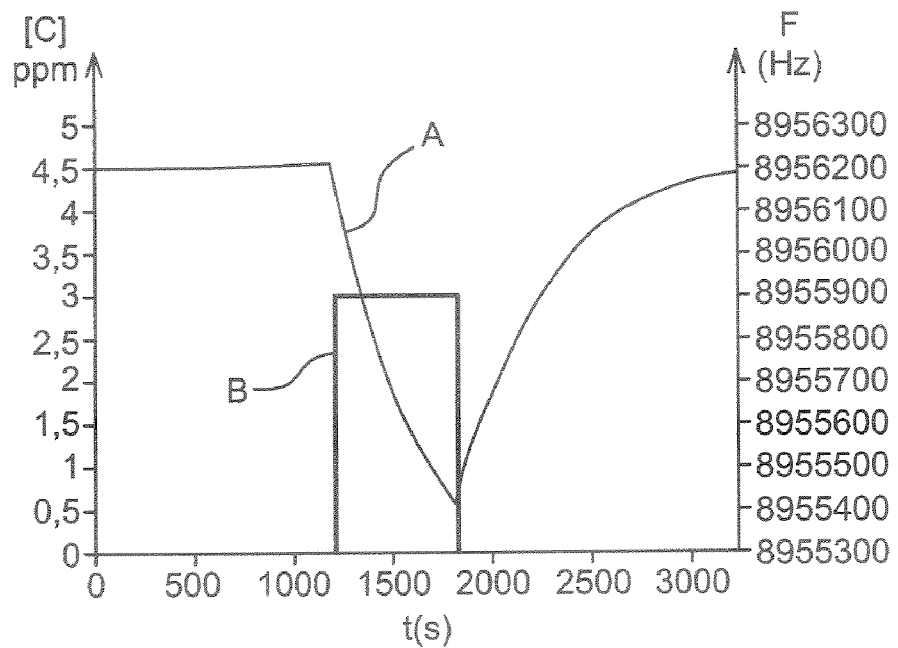
FIG. 4 represents the change in the vibration frequency of the quartz crystal of a fourth example of a sensor according to the invention when this sensor is exposed to air and to DNTFMB vapours.

FIG. 4 illustrates the change in the vibration frequency of the quartz crystal over the course of these exposures.

In this figure, curve A represents the values of the vibration frequency (F) of the quartz crystal, expressed in Hz, as a function of time (t), expressed in seconds, while curve B represents the values of the concentration of DNTFMB ([C]), expressed in ppm, also as a function of time.

Example 6

Demonstration of the Stability of the Performance Levels of a Sensor According to the Invention and of a Sensor Comprising N-allylaniline as Sensitive Material In this example, the performance levels of the sensor used in Example 3 are compared with those of a sensor having an identical structure but comprising, on each face, a film of N-allylaniline instead of the film of polymer B.

The film of N-allylaniline is deposited on each face of the quartz crystal by spraying a 10 g/l solution of this compound in chloroform 12 times, each lasting 0.5 second, in such a way as to produce a change in the vibration frequency of the quartz crystal of 2 kHz.

The two sensors are exposed for 10 minutes to DNTFMB, at a concentration of 3 ppm in air, on the day they are produced (D0) and 28 days later (D28). Between the two exposures, they are stored in ambient air with no specific conditions.

Figure 5:
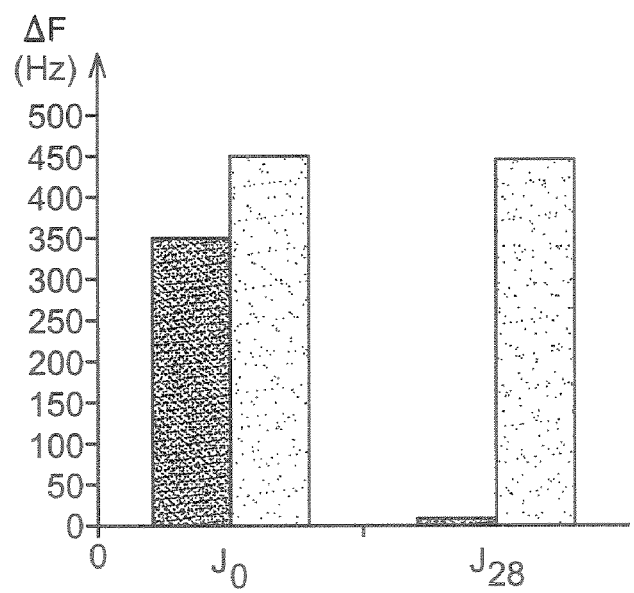
FIG. 5 represents the changes in frequency of the quartz crystals of the second example of a sensor according to the invention and a sensor comprising N-allylaniline as sensitive material, when these sensors are exposed to DNTFMB on the day they are produced (D0) and 28 days later (D28).
Figure 6:
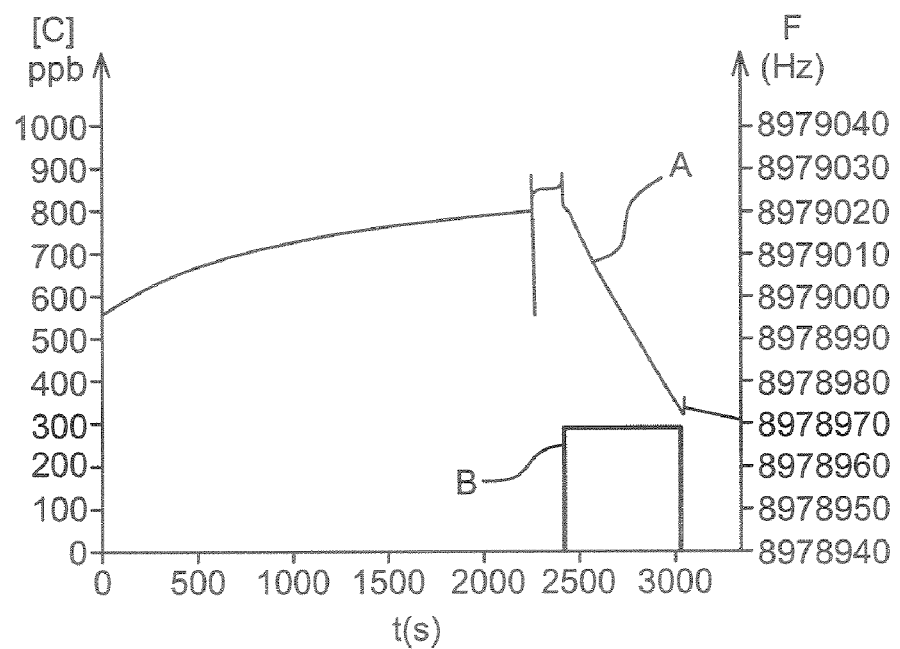
FIG. 6 represents the change in the vibration frequency of the quartz crystal of a fifth example of a sensor according to the invention when this sensor is exposed to air and to dinitrotoluene (2,4-DNT) vapour.

FIG. 5 shows the changes in vibration frequency of the quartz crystal (ΔF), expressed in Hz, obtained for the two sensors at D0 and D28, those corresponding to the sensor according to the invention being represented in light shading and those corresponding to the sensor comprising N-allylaniline as sensitive material being represented in dark shading.

Example 7

Detection of 2,4-DNT by a Sensor According to the Invention

In this example, a quartz microbalance sensor is produced by covering the two faces of a quartz crystal identical to that used in Example 2, with a thin film of polymer B prepared in accordance with Example 1.

This film is deposited on each face of the quartz crystal by spraying a 10 g/l solution of polymer B in chloroform 17 times, each lasting 0.3 second.

The change in the vibration frequency of the quartz crystal due to this coating is 9.9 kHz.

The sensor is exposed successively to:
air for 2450 seconds,
2,4-DNT at a concentration of 285 ppb in air for 600 seconds, and
air for 350 seconds,
the air and the 2,4-DNT being at ambient temperature.

FIG. 5 illustrates the change in the vibration frequency of the quartz crystal over the course of these exposures.

In this figure, curve A represents the values of the vibration frequency (F) of the quartz crystal, expressed in Hz, as a function of time (t), expressed in seconds, while curve B represents the values of the concentration of 2,4-DNT ([C]) expressed in ppb, also as a function of time.

Example 8

Comparison of the Performance Levels of a Sensor According to the Invention and of a Sensor Comprising a Thin Film of a Polysiloxane According to McGill et al (ibid)

In this example, two quartz microbalance sensors are produced, both comprising a quartz crystal identical to that used in Example 2, but differing from one another in that the quartz crystal of the first is covered on both its faces with a thin film of polymer B, whereas the quartz crystal of the second is covered with a thin film of a polysiloxane comprising units functionalized with a phenyl group substituted with two HFIP groups.

This polysiloxane corresponds to formula (VI) below:

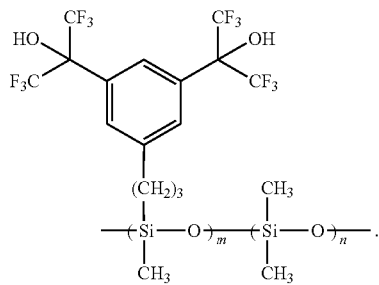

m = 47, n = 53

The films are deposited in such a way that the change in the vibration frequency of the quartz crystals due to these coatings is equal to 10 kHz for each of the sensors.

To do this, the film of polymer B is deposited on the two faces of the sensor by spraying a 5 g/l solution of polymer B in chloroform 20 times, each lasting 0.3 second, while the film of the polysiloxane of formula (VI) is deposited on the two faces of the quartz crystal by spraying a 2 g/l solution of said polysiloxane in dichloromethane 30 times, each lasting 0.2 second.

The two sensors are exposed, exactly under the same conditions to DNTFMB vapour having a concentration equal to 3 ppm, at ambient temperature and for 10 minutes.

Measurement of the vibration frequency of the quartz crystal of the two sensors at time $t_0$ and at time $t_{10min\ of}$ this exposure gives a change in the vibration frequency of 1100 Hz for the quartz crystal of the sensor according to the invention, and of 490 Hz—i.e. less than half as much—for the quartz crystal of the sensor comprising the thin film of the polysiloxane of formula (VI).

REFERENCES CITED

[1] Briglin et al., *Proceedings of SPIE*, vol 4394, 2001, 912-921,

[2] McGill et al., *Sens. Actuators B*65, 2000, 5-9,

[3] PCT WO-A-02/08314

[4] Sanchez-Pedrono et al., *Anal. Chem. Acta*, vol. 182, 1986, 285

[5] Kaufman et al., *Russian J. Org. Chem.* vol. 37, 5, 2001, 707

[6] Tsuji et al., *Chem. Lett.,* 1995, 1121-1122

The invention claimed is:

1. A method of detecting the presence of a nitro compound in a medium, the method comprising:

contacting a medium comprising a nitro compound with a chemical sensor, measuring a change in a response of the chemical sensor, and correlating the change of response to the presence of the nitro compound in the medium;

wherein the chemical sensor provides a first response when a medium does not comprise a nitro compound, wherein the chemical sensor provides a second response when a medium comprises a nitro compound, wherein the second response is different from the first response, and where the second response comprises a modification of a physical property of the sensitive material of the chemical sensor when the sensitive material contacts the nitro compound;

wherein said chemical sensor comprises:

a substrate comprising two faces;

wherein at least one of the substrate faces is covered by a thin film;

wherein the thin film comprises a sensitive material including at least one polymer comprising a siloxane repeating unit which corresponds to formula (I) below:

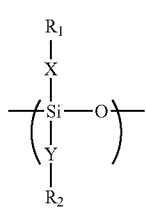
(I)

wherein
- X and Y, which may be identical or different, represent a single bond or a saturated or unsaturated, linear, branched or cyclic hydrocarbon group comprising from 1 to 30 carbon atoms and, optionally, one or more heteroatoms, and/or one or more chemical functions comprising at least one heteroatom, and/or one or more aromatic or heteroaromatic groups;
- $R_1$ represents an aniline group corresponding to formula II below:

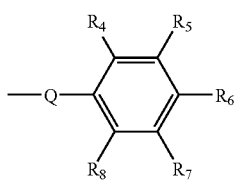
(II)

wherein
- Q represents a single bond, a —$CH_2$—group, or else an —$NR_3$—group in which $R_3$ represents a hydrogen atom or a saturated or unsaturated, linear hydrocarbon group comprising from 1 to 10 carbon atoms;
- $R_4$ to $R_8$ represent, independently of one another, a hydrogen atom, a chemical function comprising at least one heteroatom, or else a saturated or unsaturated, linear, branched or cyclic hydrocarbon group comprising from 1 to 30 carbon atoms and, optionally, one or more heteroatoms, and/or one or more chemical functions comprising at least one heteroatom, and/or one or more aromatic or heteroaromatic groups;
- wherein, when Q is a single bond or a —$CH_2$—group, then at least one of the radicals $R_4$ to $R_8$ represents an amino group —$NR_9R_{10}$ in which $R_9$ and $R_{10}$ represent, independently of one another, a hydrogen atom, a chemical function comprising at least one heteroatom, or else a saturated or unsaturated, linear, branched or cyclic hydrocarbon group comprising from 1 to 30 carbon atoms and, optionally, one or more heteroatoms, and/or one or more chemical functions comprising at least one heteroatom, and/or one or more aromatic or heteroaromatic groups;
- $R_2$ represents a hydrogen atom or an aniline of formula (II) as defined above;
- wherein the sensitive material has a physical property which is modified on contact with a chemical species; and
- wherein the chemical sensor also comprises a means for measuring a change in the physical property of the sensitive material.

2. The method according to claim 1, wherein in said chemical sensor the siloxane repeating unit corresponds to formula (I) in which $R_1$ represents a group of formula (IIa), (IIb) or (IIc) below:

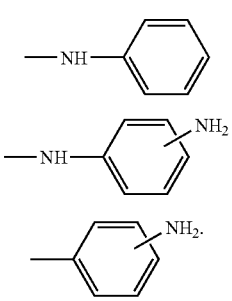

3. The method according to claim 1, wherein in said chemical sensor the siloxane repeating unit corresponds to formula (I) in which X represents an alkylene group comprising from 1 to 10 carbon atoms, Y represents an alkylene group containing from 1 to 3 carbon atoms, while $R_2$ represents a hydrogen atom.

4. The method according to claim 1, wherein in said chemical sensor the siloxane repeating unit corresponds to formula (I) in which X represents a propylene group, Y represents a methylene group, while $R_2$ represents a hydrogen atom.

5. The method according to claim 1, wherein in said chemical sensor the siloxane repeating unit corresponds to one of formulae (Ia), (Ib) and (Ic) below:

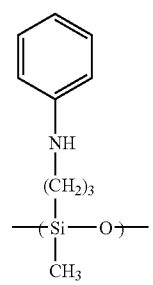
(Ia)

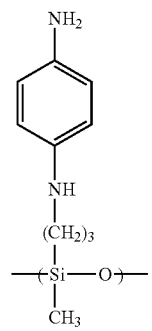
(Ib)

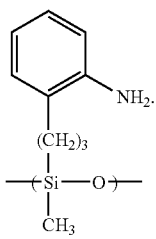
(Ic)

6. The method according to claim 1, wherein in said chemical sensor the polymer is a homopolymer.

7. The method according to claim 1, wherein in said chemical sensor the polymer is a copolymer which comprises two different siloxane repeating units, a first unit corresponding to formula (I), and a second unit corresponding to formula (III) below:

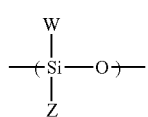

(III)

wherein W and Z, which may be identical or different, represent a hydrogen atom, or a saturated or unsaturated, linear, branched or cyclic hydrocarbon group comprising from 1 to 30 carbon atoms.

8. The method according to claim 1, wherein in said chemical sensor the second siloxane unit is a dihydrosiloxane unit, a methylhydro-siloxane unit or a dimethylsiloxane unit.

9. The method according to claim 1, wherein in said chemical sensor the polymer is a homopolymer consisting of the siloxane repeating unit of formula (Ia) below:

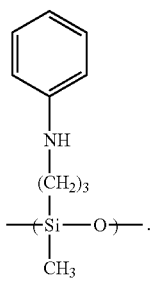

(Ia)

10. The method according to claim 1, wherein in said chemical sensor the polymer is a copolymer which comprises a first siloxane unit corresponding to formula (Ia) below:

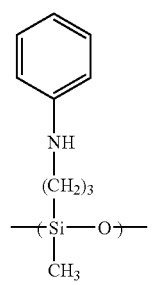

(Ia)

and a second dimethylsiloxane unit.

11. The method according to claim 1, wherein in said chemical sensor the polymer is a copolymer which comprises a first siloxane unit corresponding to formula (Ib) below:

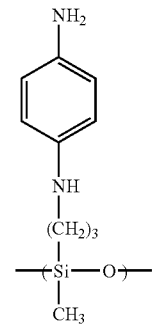

(Ib)

and a second dimethylsiloxane unit.

12. The method according to claim 1, wherein in said chemical sensor the polymer is a copolymer which comprises a first siloxane unit corresponding to formula (Ic) below:

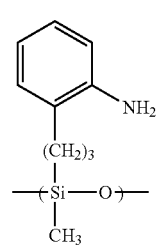

(Ic)

and a second dimethylsiloxane unit.

13. The method according to claim 1, wherein in said chemical sensor the copolymer is a random, alternating or block copolymer.

14. The method according to claim 1, wherein in said chemical sensor the first repeating unit represents, by number, approximately 47% of the repeating units forming the copolymer, while the second repeating unit represents, by number, approximately 53% of the units forming the copolymer.

15. The method according to claim 1, wherein in said chemical sensor both substrate faces are each covered by a thin film, and wherein each thin film comprises the sensitive material comprising the at least one polymer.

16. The method according to claim 1, wherein in said chemical sensor the thin film is 10 angstroms to 100 microns thick.

17. The method according to claim 1, wherein said chemical sensor is a gravimetric sensor.

18. The method according to claim 1, wherein said chemical sensor is a quartz microbalance sensor.

19. The method according to claim 1, wherein in said chemical sensor is a component of a multisensor comprising one or more individual sensors assembled together.

20. The method of claim 1, in which the nitro is selected from a nitroaromatic compound, a nitramine, a nitrosamine, a nitric ester, and combinations thereof.

21. The method of claim 20, wherein the nitro compound is in gaseous form.

22. The method of claim 1, wherein the nitro compound is selected from nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene, trinitrophenol, cyclotetramethylenetetranitramine, cyclotrimethylene-trinitramine, trinitrophenylmethylnitramine, nitrosodimethylamine, pentrite, ethylene glycol dinitrate, diethylene glycol dinitrate, nitroglycerine, nitroguanidine, and combinations thereof.

23. The method of claim 1, for detecting explosives.

* * * * *